US006989143B1

(12) United States Patent
Park et al.

(10) Patent No.: US 6,989,143 B1
(45) Date of Patent: Jan. 24, 2006

(54) DEPLETION METHOD OF BLOOD PLASMA ASCORBATE

(75) Inventors: Chan Hyung Park, 611 S. 291st St., Federal Way, WA (US) 98003; Yong C. Boo, Birmingham, AL (US)

(73) Assignees: Jin Yang Pharm Co., Ltd., Seoul (KR); Chan Hyung Park, Federal Way, WA (US)

( * ) Notice: Subject to any disclaimer, the term of this patent is extended or adjusted under 35 U.S.C. 154(b) by 0 days.

(21) Appl. No.: 10/275,195

(22) PCT Filed: May 2, 2000

(86) PCT No.: PCT/KR00/00415

§ 371 (c)(1),
(2), (4) Date: Oct. 31, 2002

(87) PCT Pub. No.: WO01/82955

PCT Pub. Date: Nov. 8, 2001

(51) Int. Cl.
*A61K 38/44* (2006.01)
(52) U.S. Cl. ..................................... 424/94.4; 435/181
(58) Field of Classification Search ............... 424/94.4; 435/181
See application file for complete search history.

(56) References Cited

U.S. PATENT DOCUMENTS 5,834,273 A     11/1998  Futatsugi et al.

FOREIGN PATENT DOCUMENTS

DE        30 43 529       6/1982
JP        011287686    *  5/1989

OTHER PUBLICATIONS

JPAB Abstract of JP01128786 Published May 22, 1989.*
DWPI Abstract of JP01128786 Published May 22, 1989.*
Sakagami, et al., "Effect of Ascorbate Oxidase on Radical Intensity and Cytotoxic Activity of Ascorbate", Anticancer Res., Jan., 1997, 7 (2A), 1163-1166.
Park, et al., "Ascorbic Acid: A Culture Requirement of Colony Formation by Mouse Plasmacytoma Cells", Science 1764: 720-722, 1971.
Park, "Studies of growth characteristics of myeloma in vitro", Ph.D. Thesis, University of Toronto, 1971.
Park, et al. "Improved Growth of in Vitro Colonies in Human Acute Leukemia with the Feeding Culture Method", Cancer Research 37:4595-4601, 1977.
Park, et al, "Analysis of the growth Enhancing Effect of L-Ascorbic Acid on Human Leukemic Cells in Culture", Exptl Hematol 8:853-859, 1980.
Park, et al, "In Vitro Growth Modulation by L-Ascorbic Acid of Colony-forming Cells from Bone Marrow of Patients with Myelodysplastic Syndromes", Cancer Research 52:4458-4466, 1992.

Stadtman, et al., "Reactive Oxygen-Mediated Protein Oxidation in Aging and Disease", Chem Res Toxicol 10: 485:494, 1997.
Levine, et al., "Does vitamin C having a pro-oxidant effect?" Nature 395:231-232, 1998.
Sakagami, et al., "Modulating Factors of Radial Intensity and Cytotoxic Activity of Ascorbate (Review)", Anticancer Research 17:3513-3520, 1997.
Sauberlich, et al., "Pharmacology of Vitamin C", Annu. Rev. Nutr. 14: 371-391, 1994.
Halliwell, et al., "Antioxidant and Prooxidant Properties of Vitamin C", Paker, L: Fuchs, J., eds. Vitamin C in health and disease, New York: Marcel Dekker Inc., 1997 59-73.
Frei, et al., "Ascorbate is an outstanding antioxidant in human blood plasma", Proc. Natl. Acad. Sci., 86:6377-6381, 1989.
Niki, "Action of ascorbic acid as a scavenger of active and stable oxygen radicals", Am J Clin Nutr 1991, 54:1119S-24S.
Mendiratta, et al., "Erythrocyte Ascorbate Recycling: Antioxidant Effects in Blood", Free Radic. Biol. Med. 24: 789797, 1998.
Bendich, et al., "The Health Effects of Vitamin C Supplementation: A Review", J. Am. Coll. Nutr. 14: 124-136, 1995.
Block, "Vitamin C Status and Cancer. Epidemiologic Evidence of Reduced Risk", Ann. NY Acad. Sci., 669: 280-290, 1992.
Bram, et al., "Vitamin C preferential toxicity of Malignant melanoma cells", Nature, 284: 629-631, 1980.

(Continued)

*Primary Examiner*—Herbert J. Lilling
(74) *Attorney, Agent, or Firm*—Merchant & Gould P.C.

(57) ABSTRACT

Artificial modulation of ascorbate level was investigated in mice capable of de novo synthesis of ascorbate. When mice were given exogenous ascorbate or its physiological precursor, L-gulono-γ-lactone, the plasma level of ascorbate was elevated substantially but immediately returned to the basal levels. Comparably, the administration of ascorbate oxidase caused a rapid disappearance of plasma ascorbate but followed by an immediate restoration of ascorbate. These results indicate the difficulties encountered in the modulation of ascorbate level in the animal. However, the circulation life of the exogenous ascorbate oxidase in the animal was successfully extended by chemical modification with methoxypolyethylene glycol. The modified enzyme retained a full activity and exerted a remarkably prolonged depletion of plasma ascorbate compared with the native enzyme. This study suggests that the chemically modified ascorbate oxidase should find many uses in the animal studies on ascorbate since it was found to deplete plasma ascorbate even in the ascorbate-synthesizing animal in the absence of dietary control. The enzyme should prove to be useful in tumor control because there are tumor systems in mice and man amenable to the manipulation of ascorbate level.

3 Claims, 4 Drawing Sheets

OTHER PUBLICATIONS

Figure 1:
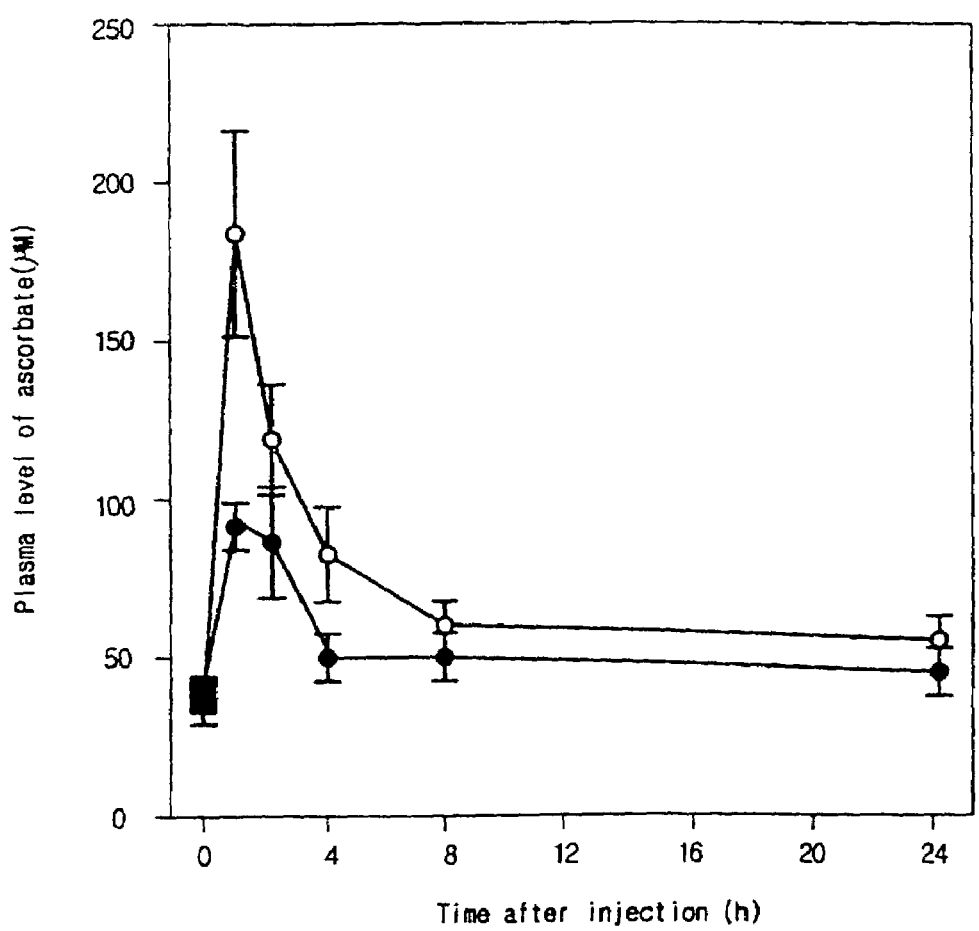

Riordan, et al, "Intravenous Ascorbate as a Tumor Cytotoxic Chemotherapeutic Agent", Med. Hypothesis, 44: 207-213, 1995.

Koh, et al., "Differential Effects and Transport Kinetics of Ascorbate Derivatives in Leukemic Cell Lines", Anticancer Res., 19: 2487-2494, 1998.

Park, et al, "Growth modulation of human leukemic, preleukemic, and myeloma progenitor cells by L-ascorbic acid", Am. J. Clin. Nutr., 54: 1241S-1246S, 1991.

Tsao, et al., "Effect of Dietary Ascorbic Acid Intake on Tissue Vitamin C in Mice", J. Nutr., 117: 291-297, 1987.

Jackson, et al., "Synthesis, Isolation and Characterization of Conjugates of Ovalbumin with Monomethoxypolyethylene Glycol Using Cyanuric Chloride as the Coupling Agent", Anal. Biochem., 165: 114-127, 1987.

Laemmli, "Cleavage of Structural Proteins during the Assembly of the Head of Bacteriophage T4", Nature, 227: 680-685, 1970.

Kim, et al., "A Heme-containing Ascorbate Oxidase from *Pleurotus ostrealtus*" J. Biol. Chem., 271: 3105-3111, 1996.

Bánhegyi, et al., "Ascorbate Metabolism and it Regulation in Animals", Free Radic. Biol. Med., 23: 793-803, 1997.

Nishikimi, et al., "L-Gulono-γ-lactone Oxidase (Rate and Goat Liver)", Methods Enzymol., 62: 24-30, 1979.

Nishikimi, et al.Cloning and Chromosocmal Mapping of the Human Nonfunctional Gene for L-Gulono-γ-lactone Oxidase, the Enzyme for L-Ascorbic Acid Biosynthesis Missing in Man, J. Biol. Chem., 269: 13685-13688, 1994.

Braun, et al., "Ascorbate as a Substrate for Glycolysis or Gluconeogenesis: Evidence for an Interorgan Ascorbate Cycle", Free Radic. Bil. Med., 23: 804-808, 1997.

Tsao, et al., "Effect of Exogenous Ascorbic Acid intake on Biosynthesis of Ascorbic Acid in Mice", Life Sci., 45: 1553-1557, 1989.

Lee, et al., "Axcorbate Oxidase", Methods Enzymol., 62: 30-39, 1979.

Stevanato, et al., "Determinationof Ascorbic Acid with Immobilizd Green Zucchini Ascorbate Oxidase", Anal. Biochem, 149: 537-542, 1985.

Himmelrcich, et al., "C NMR Studies of Vitamin C Transport and its Redox Cycling in Human Erythrocytes", Biochemistry, 37: 7578-7588, 1998.

Abuchowski, et al., "Effect of Covalent Attachment of Polyethylene Glycol on Immunogenicity and Circulating Life of Bovine Liver Catalase", J. Bio. Chem., 252: 3582-3586, 1977.

Duncan, et al., Polymer Conjugates. Pharmacokinetic Considerations for Design and Development, Clin. Pharmacokinet, 27: 290-306, 1994.

Koshiishi et al., "Degradation of dehydroascorbate to 2,3-diketogulonate in blood circulation", Biochim. Biophys. Acta., 1425: 209-214, 1998.

* cited by examiner

DEPLETION METHOD OF BLOOD PLASMA ASCORBATE

FIELD OF THE INVENTION

The present invention relates to a effective depletion method of blood plasma ascorbate, by using ascorbate oxidase modified with biologically inert polymers.

DESCRIPTION OF THE PRIOR ART

<Desirability of L-ascorbic acid(LAA) in vivo manipulation for Pre-Leukemia(Myelodysplastic Syndromes, MDS) and Acute Myeloid Leukemia(AML): overall perspectives and >

LAA has been shown to be an essential requirement for the growth of mouse myeloma cells in an in vitro colony assay(1). When this finding was applied to human myeloma, there appeared a similar effect although it was hard to test because human myeloma cell colonies do not grow well in vitro(2). Human leukemia(AML) cell colonies grow well in our daily-feeding agar culture system(3), and an early study indicated that LAA modulated growth of leukemic cells in approximately ½ of a small number of patients(4). This has been confirmed in a large number of patients.

All these findings considered together indicate that leukemic cells sensitive to LAA in vitro may well be amenable to in vivo manipulation of LAA.

Most previous studies on the in vitro LAA effect were performed on leukemia (AML) cells. A more recent study indicates that the pre-leukemia, or myelodysplastic syndromes(MDS) generally considered to be related to AML, has virtually an identical pattern in terms of LAA sensitivity, with 30% showing growth enhancement and 16% suppression with LAA(5).

<The recent lessons from a first patient subjected to LAA in vivo manipulation and multiple other patients from another independent group: the case for LAA supplementation>

The straightforward approach, exploiting above information clinically, to the patients in whom leukemic cell growth is enhanced by LAA would naturally be in vivo depletion of LAA. A first patient was had on IRB(International Review Board)-approved protocol focusing on LAA depletion and, indeed this patient appears to have had delay in relapse of leukemia by LAA depletion. However, the patient finally relapsed showing the beginning of rapid rise in peripheral blast counts. There then was no choice but gradually increasing the dose of LAA in the hope of increasing benefit, and that can suppress disease over 10 weeks.

<Inference from above rationales and experiences leading to cyclic application of bipolar approaches with extreme supplementation and extreme depletion>

It is compelling that high dose LAA indeed can suppress human malignancies. It is also believed that the case had benefit during LAA depletion phase also by having prolonged period(12 wks) before frank relapse, a consequence logically expected from the fact that patient's leukemic cells growth was enhanced by LAA.

This kind of bipolar response is not unprecedented in treatment of human malignancies. In fact LAA is commonly known as an antioxidant but can become the other extreme, prooxidant at least in vitro(6,7), depending for example on metallic ion concentration around(8). This can be one possible explanation for this bipolar activities. The extreme lack of LAA may well be the situation of absence of antioxidant protection with endogenous and ubiquitous oxidants damaging cells unopposed. The extreme high level of LAA with some other intra/extra cellular status(again such as Fe++) may render it prooxidant leading to cell damage. Whatever mechanism might be, the dose response study with extension into high dose levels proves this bipolar inhibition on the leukemic cell growth of this first patient.

DISCLOSURE OF THE INVENTION

It is clear that ascorbate has effects on many physiological processes in humans [1]. Insufficient intake of ascorbate causes scurvy associated with decreased collagen synthesis. Ascorbate influences on wound healing, gastric iron uptake, and many immunological and biochemical reactions. Apparently, most, if not all, of ascorbate's functions are related to the reducing property of ascorbate keeping metal ions in reduced state. As a reductant, ascorbate can act either as an antioxidant or as a prooxidant in aqueous environments [2]. However, ascorbate is generally designated as an important antioxidant for humans based on many in vitro findings [3–5]. Further, it is widely held that ascorbate may contribute to the prevention of pathological processes associated with oxidative injury, but only circumstantial evidence is available [6, 7].

Ascorbate has also been implicated to affect the growth of animal cells in vitro [8–11]. The effect appears as either stimulatory or inhibitory depending on the cells. Although the precise mechanism for the growth modulation by ascorbate is not known, the effect has been proven to be biological rather than physicochemical since optical isomers of ascorbate or other redox compounds are without effect. Further, it is worthy to note that malignant cells are more sensitive than normal counterparts to the ascorbate effects. We have shown the unusual ascorbate sensitivity of malignant cells from patients with acute myelogenous leukemia and myelodysplastic syndromes [12, 13].

There are compelling evidences that this in vitro effect will translate to in vivo situation ultimately resulting in tumor control. As explained fully in the Description of the Prior Art, both extreme depletion and supplementation will be beneficial to the control of cancer. Therefore the depletion and supplementation periods will need to be cycled. One step further, for depletion to be maximumly effective prior supplementation period will be desirable and vice versa. In this Application one of these 2 extremes, depletion, is the subject.

Animal studies are critical for the demonstration of the physiological relevance of many proposed functions of ascorbate. For the experimental purpose, ascorbate level in animals needs to be modulated artificially but dietary controls are not so promising [14]. Ascorbate administered in excess is readily excreted from the body and only minor fraction is equilibrated with body stores of ascorbate. Furthermore, such laboratory animals as mice are capable of endogenously synthesizing ascorbate, and by nature they are insensitive to dietary intake of ascorbate. The importance of animal studies on ascorbate modulation as related to tumor control, and the usefulness of mice as laboratory animals prompted us to investigate new methods of ascorbate modulation in mice. Two opposite methods are investigated in the present study, one for the elevation of ascorbate level and another for the selective depletion of ascorbate.

BRIEF DESCRIPTION OF THE ATTACHED DRAWINGS

The above and other objects, features and other advantages of the present invention will be more clearly understood from the following detailed description taken in conjunction with the accompanying drawings, in which:

FIG. 1. Time-dependent changes of plasma ascorbate level in mice given sodium ascorbate (-o-) and L-gulono-γ-lactone (-•-). Drugs were dissolved in distilled water and administered by intraperitoneal injections, both at 5 mmole/kg. Blood was taken from each animal time-sequentially for the assay of plasma ascorbate with HPLC-ECD, as described in MATERIALS AND METHODS. Zero time control animals were given 0.2 ml of normal saline. Data represent Mean±SD (n=3–5).

Figure 2:
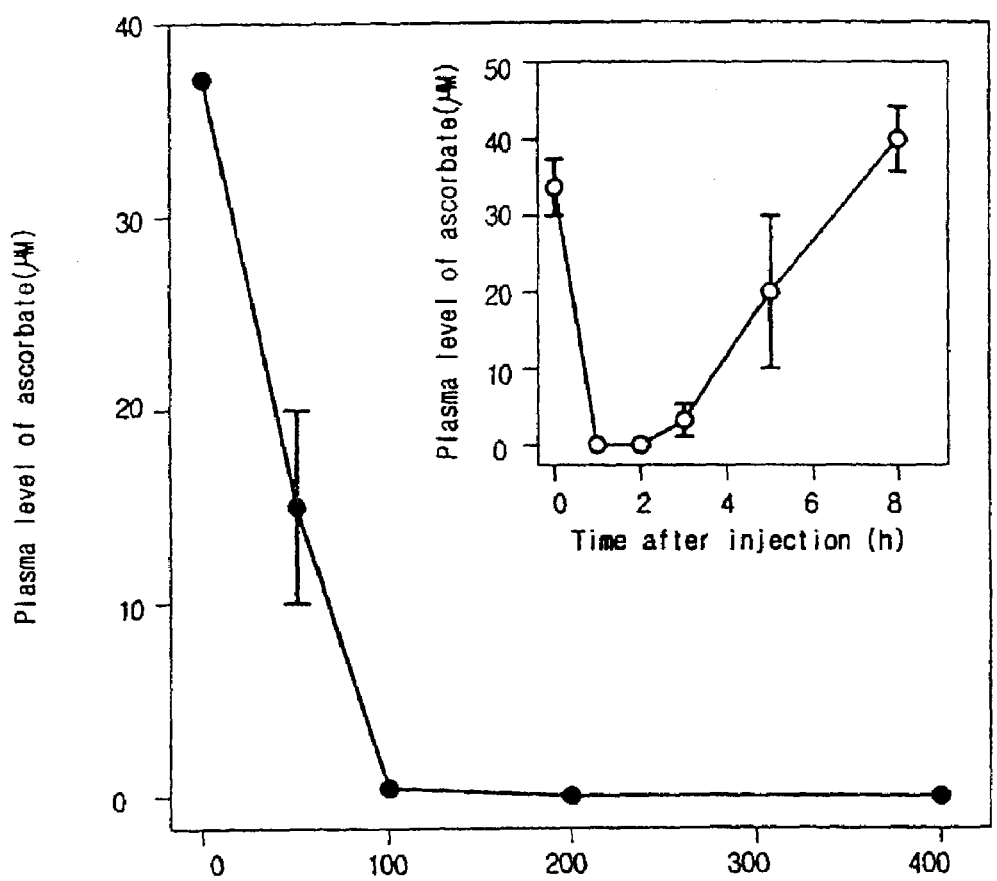

FIG. 2. Effects of exogenous ascorbate oxidase on plasma ascorbate level in mice. Ascorbate oxidase in normal saline was intravenously administered into BALB/c mice at various doses. Control animals were given 0.1 ml of normal saline. Plasma ascorbate level was assayed one hour after drug administration. Inset shows the time-dependent change of plasma ascorbate level in mice given 400 units/kg of ascorbate oxidase. Data represent Mean±SD (n=3–5).

Figure 3:
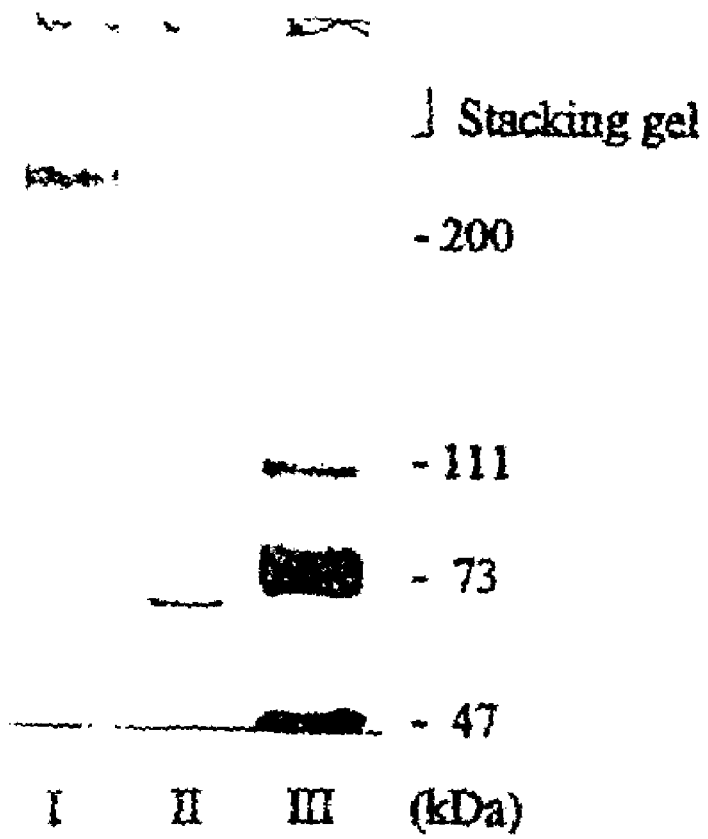

FIG. 3. SDS-PAGE of the modified ascorbate oxidase and the unmodified. Electrophoresis was performed on 6% gel and proteins were stained with Coomassie Blue. Lane I, ascorbate oxidase coupled to mPEG; lane II, ascorbate oxidase; lane III, standard molecular weight markers consisted of myosin H chain (200 kDa), phosphorylase (111 kDa), bovine serum albumin (73 kDa) and ovalumin (47 kDa).

Figure 4:
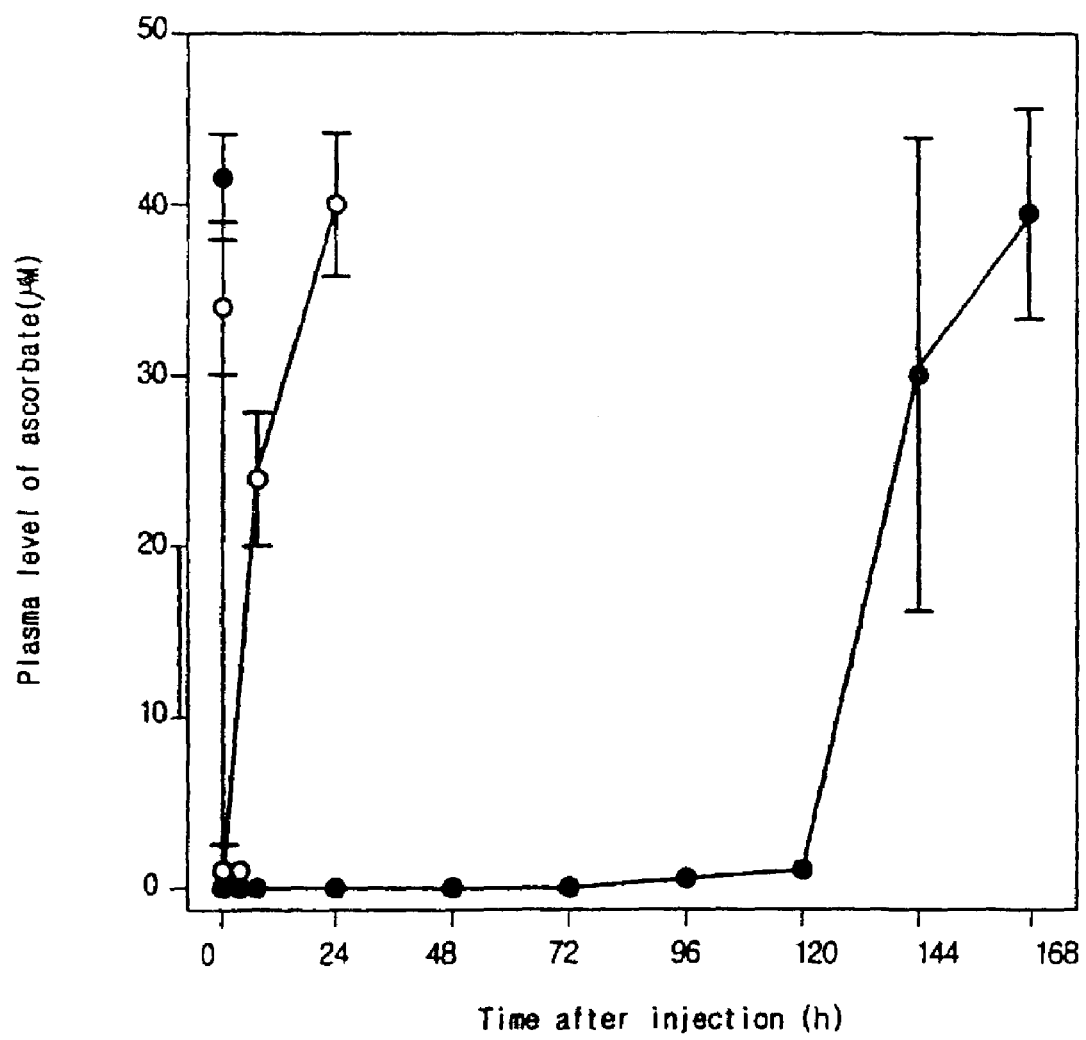

FIG. 4. Comparison of ascorbate depletion in mice given native ascorbate oxidase (-o-) and ascorbate oxidase coupled to mPEG (-•-). Drugs in normal saline were administered via intraperitoneal routes, both at 400 units/kg. Control animals were given 0.1 ml of normal saline. Data represent Mean±SD (n=3–5).

MODES FOR CARRYING OUT THE INVENTION

Materials and Methods

Materials used in this invention are as follows.

Sodium ascorbate, L-gulono-γ-lactone, ascorbate oxidase (from *Curcubita* species), methoxypolyethylene glycol (mPEG) activated with cyanuric chloride (average molecular weight 5000), borax, sodium citrate, mataphosphoric acid and dithiothreitol were purchased from SIGMA (St. Louis, Mo.). All other chemicals are of reagent grade.

Chemical modification of ascorbate oxidase is as follows.

Ascorbate oxidase (EC 1.10.3.3)) was modified with MPEG activated with cyanuric chloride, as in Jackson et al. [15]. Briefly describing, 4 mg of ascorbate oxidase was dissolved in 10 ml of ice-cold 0.1 M borax buffer (pH 9.2) and then 200 mg of activated mPEG was directly added to the enzyme solution with stirring on ice. The reaction mixture was kept on ice for 60 min and dialyzed against normal saline at 4° C. across a Spectrapor-2 membrane (SPECTRUM. Houston, Tex.). The dialyzed protein, i.e. pegylated ascorbate oxidase, was used immediately or stored at −60° C. until used.

Sodium dodecyl sulphate-polyacrylamide gel electrophoresis (SDS-PAGE) was performed on 6% gel prepared by Laemmli's formulation [16] and proteins were stained with Coomassie Blue. Ascorbate oxidase activity was assayed spectrophotometrically, as in Kim et al. [17].

Animals used in this invention are as follows.

Specific pathogen-free female BALB/c mice (body weight, ca. 25 g) were used in the present study. Animals were obtained from Dae-Han Laboratory Animal Center (Daejeon, Korea) and cared for according to the ILAR guidelines in the animal care facility of Samsung Biomedical Research Center (Seoul, Korea). They were fed a diet from Jell Laboratory Chow (Seoul, Korea). Feed and water were offered ad libitum.

Extraction and assay of ascorbate are as follows.

The animal was anesthetized with diethyl ether vapour and blood was obtained by choroidal venous plexus. About one ml of blood was collected into a microcentrifuge tube that contained 50 $\mu$l of 130 mM sodium citrate as an anticoagulant. The blood was centrifuged at 1000×g for 10 min to obtain plasma, which was rapidly cooled on ice. Equal volume of ice-cold 10% metaphosphoric acid was added to the plasma and the mixture was centrifuged at 10000×g for 10 min. The ascorbate content in the supernatant was measured directly by HPLC method. An aliquot of the sample was treated with 100 mM dithiothreitol at neutral pH to reduce dehydroascorbate to ascorbate, and then total ascorbate content was measured. The content of dehydroascorbate was estimated from the difference between the two measurements. In some cases, blood plasma was directly ultrafiltrated by using a Microcon YM-10 centrifugal filter device (MILLIPORE, Bedford, Mass.), as described by Mendiratta et al. [5]. The ultrafiltrate was injected to HPLC either directly for the assay of ascorbate, or after incubation with dithiothreitol for the assay of total ascorbate (ascorbate plus dehydroascorbate).

Ascorbate was assayed by HPLC with the electrochemical detection, as previously described [11]. HPLC system (SHIMADZU, Tokyo, Japan) consisted of CBM-10A communication module, LC-10AD pump, SIL-10A auto injector, CTO-10A column oven, and L-ECD-6A electrochemical detector. Separation was carried out on a Shim-pack CLC-ODS column (6 mm×15 cm) with a guard column of the same material (4 mm×1 cm). Mobile phase was 50 mM potassium phosphate (pH 2.5) containing 1 mM EDTA, eluted at a flow rate of 1.0 ml/min. The potential of the glassy carbon working electrode was set at +0.6 V versus an Ag/AgCl reference electrode.

Data analysis is as follows. Statistical software package StatView 4.0 (Abacus concepts, Berkeley, Calif.) was used for the data analysis.

Results and Discussion

Ascorbate is synthesized from glucose via the hexuronic acid pathway in ascorbate synthesizing animals [18]. L-Gulono-γ-lactone is an immediate precursor of ascorbate and its conversion into ascorbate is catalyzed by L-gulono-γ-lactone oxidase [19]. Human's inability to synthesize ascorbate is due to the lack of this enzyme [20]. As a physiological precursor of ascorbate, L-gulono-γ-lactone might be useful for the elevation of ascorbate level in ascorbate-synthesizing animals including mice. This notion was subjected to experimental scrutiny in the present study (FIG. 1). When mice were given 5 mmole/kg of L-gulono-γ-lactone, there was a substantial increase in plasma level of ascorbate, in agreement with the capacity of the animal to synthesize ascorbate. However, the accumulated ascorbate rapidly diminished to normal levels within a few hours, similarly to the directly administered ascorbate (as sodium salt, 5 mmole/kg), implicating that the animal has the capacity to keep ascorbate level from abnormal elevation. Plausible mechanisms may include the renal excretion and metabolic consumption of excessive ascorbate [14, 21], and inhibition of L-gulono-γ-lactone oxidase by ascorbate [22]. All these mechanisms would be beneficial for the life of mice, but due to these mechanisms, we have hardly a chance to investigate the physiological consequences of ascorbate elevation in the laboratory animal.

Ascorbate oxidase is an enzyme that catalyzes the oxygen-dependent oxidation of ascorbate to dehydroascorbate [23]. Due to the high substrate specificity and catalytic efficiency, the enzyme has widely been used in numerous in vitro studies on ascorbate, including selective determination of ascorbate [23]. However, its compatibility with animal systems is unknown. The enzyme was tested as a drug for the selective depletion of ascorbate in the present study. As shown in FIG. 2, the administration of ascorbate oxidase into mice lowered plasma level of ascorbate in a dose-dependent manner. The ascorbate depletion was not observed when the enzyme was heat-inactivated (data not shown). These results implicate a competition in the blood between the activity of exogenous ascorbate oxidase and the ascorbate maintenance mechanisms, such as ascorbate regeneration from dehydroascorbate by red blood cells [5, 25] and ascorbate release from the liver where de novo synthesis of ascorbate takes place [18]. The minimal dose of ascorbate oxidase inducing a total clearance of plasma ascorbate appeared to be about 100 units/kg equivalent to 1 $\mu$g protein/animal, indicating the effectiveness of ascorbate oxidase in the blood. Time-sequential monitoring of the ascorbate level in mice given 400 units/kg of ascorbate oxidase, however, revealed a rapid restoration of plasma ascorbate, probably associated with short circulation life of the exogenous enzyme.

Enzymes can be chemically modified with retention of activities by attaching biologically inert polymers at sites other than the active site. Such chemical modifications have been shown to prolong the circulation life of the enzymes in animals, by eliminating immunogenicity of native proteins and/or reducing the renal excretion [26, 27]. mPEGs are very useful polymers in this respect and readily can be attached to proteins by use of cyanuric chloride as a coupling agent [15]. Ascorbate oxidase could be chemically modified with cyanuric chloride-activated mPEG in the present study. A far excessive amount of the activated mPEG (1000 molecules per one enzyme molecule) was used to ensure the reaction. The attachment of the polymers to the enzyme was verified through SDS-PAGE (FIG. 3). The modified ascorbate oxidase exhibited a very slow mobility on 6% gel compared with the unmodified. The former appeared as a broad band close to the stacking gel, whereas the latter occurred as a sharp band with apparent molecular weight of 70 kDa corresponding to the subunit [23]. Enzyme activity loss by the modification was very slight (less than 10%).

To assess the influence of chemical modification, mice were given either native ascorbate oxidase or the modified enzyme, both at 400 unit/kg, and plasma level of ascorbate was monitored time-sequentially. Drugs were administered via intraperitoneal injections that were found effective as intravenous routes. As shown in FIG. 4, the modified enzyme exerted a rapid clearance of plasma ascorbate as the native enzyme, in line with its retention of enzyme activity. Furthermore, the duration of ascorbate depletion was remarkably prolonged; the modified enzyme depleted for about 120 h compared with 3–4 h for the native enzyme. These results clearly demonstrate the benefit of chemical modification to extend the circulation life and the action time of the exogenous enzyme in animals.

Ascorbate is just oxidized to dehydroascorbate by the activity of ascorbate oxidase. Nonetheless, any trace amount of dehydroascorbate was not detected in plasma during the ascorbate depletion (data not shown). At least two different methods of sample preparation employed in the present study gave the same results. The results are not surprising, however, since dehydroascorbate is known to be very unstable in plasma [28]. Although further studies are required, it is tentatively inferred that the modified ascorbate oxidase may lead a rather comprehensive depletion of plasma ascorbate including its oxidized form, by steadily oxidizing available ascorbate to dehydroascorbate which decomposes subsequently.

In summary, the present paper describes two different approaches to attain the purpose of ascorbate modulation in mice capable of de novo synthesis of ascorbate. In the first trial, we tested the administration of L-gulono-γ-lactone as a physiological precursor of ascorbate to elevate ascorbate level, but no significant merits over direct ascorbate supplementation were observed. However, in the following trial, the exogenous ascorbate oxidase was found very effective for the depletion of plasma ascorbate. The catalytic efficiency of the enzyme appeared to compete readily with the ascorbate synthesis and/or recycling mechanisms in animals. Employing a biologically inert polymer to the enzyme, we could surmount the problem associated with the short circulation life of the exogenous enzyme. The chemical modification of enzyme did not require additional risks such as severe loss of enzyme activity or toxicity to animals. The modified ascorbate oxidase should find numerous uses in vivo researches on ascorbate. Notably, it seems likely to be used in animal studies to demonstrate physiological relevancy of many in vitro findings such as antioxidant actions of ascorbate [3–5]. The most straight-forward application will be the growth retardation of malignant cells sensitive to ascorbate[8, 11–13], ultimately leading to the control of malignancies.

REFERENCES (1) Park CH, Bergsagel DE, McCulloch EA: Ascorbic acid: A culturerequirement for colony formation by mouse plasmacytoma cells. Science 174:720–722, 1971

(2) Park CH: Studies of growth characteristics of myeloma in vitro, Ph.D. Thesis, University of Toronto. 1971

(3) Park CH, Savin MA, Hoogstraten B, Amare M, Hathaway P: Improved growth of in vitro colonies in human acute leukemia with the feeding culture method. Cancer Research 37:4595–4601, 1977

(4) Park, CH, Amare M, Hoogstraten B: Analysis of the growth enhancing effect of L-ascorbic acid on human leukemic cells in culture. Exptl Hematol 8:853–859, 1980

(5) Park CH, Kimler BF, Bodensteiner D, Lynch SR, Hassanein RS: In vitro growth modulation by L-ascorbic acid of colony-forming cells from bone marrow of patients with myelodysplastic syndromes. Cancer Research 52:4458–4466, 1992

(6) Stadtman ER, Berlett BS: Reactive oxygen mediated protein oxidationin in aging and disease. Chem Res Toxicol 10:485–494, 1997

(7) Levine M, Daruwala RC, Park JB, Rumsey SC. Wang Y: Does vitamin C have a pro-oxidant effect? Nature. 395: 231–232,1998

(8) Sakagami H, Satoh K: Modulating factors of radical intensity and cytotoxic activity of ascorbate(review). Anticancer Research 17:3513–3520, 1997

[1] Sauberlich, H. E. Pharmacology of vitamin C. Annu. Rev. Nutr. 14: 371–391; 1994.

[2] Halliwell, B.; Whiteman, M. Antioxidant and prooxidant properties of vitamin C. In: Packer, L.; Fuchs, J., eds. Vitamin C in health and disease. New York: Marcel Dekker Inc.; 1997: 59–73.

[3] Frei, B.; England, L.; Ames, B. N. Ascorbate is an outstanding antioxidant in human blood plasma. Proc. Natl. Acad. Sci. USA. 86: 6377–6381; 1989.

[4] Niki, E. Action of ascorbic acid as a scavenger of active and stable oxygen radicals. Am. J. Clin. Nutr. 54:1119S–1124S; 1991.

[5] Mendiratta, S.; Qu, Z.; May, J. M. Erythrocyte ascorbate recycling: Antioxidant effects in blood. Free Radic. Biol. Med. 24: 789–797; 1998.

[6] Bendich, A.; Langseth, L. The health effects of vitamin C supplementation: a review. J. Am. Coll. Nutr. 14: 124–136; 1995.

[7] Block G. Vitamin C status and cancer: epidemiologic evidence of reduced risk. Ann. NY Acad. Sci. 669: 280–290; 1992.

[8] Park, C. H.; Bergsagel, D. E.; McCulloch, E. A. Ascorbic acid: a culture requirement for colony formation by mouse plasmactoma cells. Science 174: 720–722; 1971.

[9] Bram, S.; Froussard, P.; Guichard, M.; Jasmin, C.; Augery, Y.; Sinoussi-Barre, F.; Wray, W. Vitamin C preferential toxicity for malignant melanoma cells. Nature 284: 629–631; 1980.

[10] Riordan, N. H.; Riordan, H. D.; Meng, X.; Li, Y.; Jackson, J. A. Intravenous ascorbate as a tumor cytotoxic chemotherapeutic agent. Med. Hypothesis 44: 207–213; 1995.

[11] Koh, W. S.; Lee, S. J.; Lee, H.; Park, C.; Park, M. H.; Kim, W. S.; Yoon, S. S.; Park, K.; Park, C. H. Differential effects and transport kinetics of ascorbate derivatives in leukemic cells. Anticancer Res. 18: 2487–2494; 1998.

[12] Park, C. H.; Kimler B. F. Growth modulation of human leukemic, preleukemic, and myeloma progenitor cells by L-ascorbic acid. Am. J. Clin. Nutr. 54: 1241S–1246S; 1991.

[13] Park, C. H.; Kimler, B. F.; Bodensteiner, D.; Lynch, S. R.; Hassanein, R. S. In vitro growth modulation by L-ascorbic acid of colony forming cells from bone marrow of patients with myelodysplastic syndromes. Cancer Res. 52: 4458–4466; 1992.

[14] Tsao, C. S.; Leung, P. Y.; Young, M. Effect of dietary ascorbic acid intake on tissue vitamin C in mice. J. Nutr. 117: 291–297; 1987.

[15] Jackson, C-J. C.; Charlton, J. L.; Kuzminski, K.; Lang, G. M.; Sehon, A. H. Synthesis, isolation, and characterization of conjugates of ovalbumin with monomethoxypolyethylene glycol using cyanuric chloride as coupling agent. Anal. Biochem. 165: 114–127; 1987.

[16] Laemmli, U. L. Cleavage of structural protein during the assembly of the head of bacteriphage T4. Nature 227: 680–685; 1970.

[17] Kim, Y-R.; Yu, S-W.; Lee, S-R.; Hwang, Y-Y.; Kang, S-O. A heme-containing ascorbate oxidase from *Pleurotus ostreatus*. J. Biol. Chem. 271: 3105–3111; 1996.

[18] Bánhegyi, G.; Braun, L.; Csala, M.; Puskás, F.; Mandl, J. Ascorbate metabolism and its relation in animals. Free Radic. Biol. Med. 23: 793–803; 1997.

[19] Nishikimi, M. L-Gulono-γ-lactone oxidase (rat and goat liver). Methods Enzymol. 62: 24–30; 1979.

[20] Nishikimi, M.; Fukuyama, R.; Minoshima, S.; Simizu, N.; Yagi, K. Cloning and chromosomal mapping of the human nonfunctional gene for L-gulono-γ-lactone oxidase, the enzyme for L-ascorbic acid biosynthesis missing in man. J. Biol. Chem. 269: 13685–13688; 1994.

[21] Braun, L.; Puskás, F.; Csala M.; Mészáros, G.; Mandl, J.; Bánhegyi, G. Ascorbate as a substrate for glycolysis or gluconeogenesis: evidence for an interorgan ascorbate cycle. Free Radic. Biol. Med. 23: 804–808; 1997.

[22] Tsao, C. S.; Young, M. Effect of exogenous ascorbic acid intake on biosynthesis of ascorbic acid in mice. Life Sci. 45: 1553–1557; 1989.

[23] Lee, M. H.; Dawson, C. R. Ascorbate oxidase. Methods Enzymol. 62: 30–39; 1979.

[24] Stevanato, R.; Avigliano, L.; Finazzi-Agro, A. Determination of ascorbic acid with immobilized green zucchini ascorbate oxidase. Anal. Biochem. 149: 537–542; 1985.

[25] Himmelreich, U.; Drew, K. N.; Serianni, A. S.; Kuchel, P. W. $^{13}$C NMR studies of vitamin C transport and its redox cycling in Human Erythrocytes. Biochemistry 37: 7578–7588; 1998.

[26] Abuchowski, A.; McCoy, J. R.; Palczuk, N. C.; van Es, T.; Davis, T. F. Effect of covalent attachment of polyethylene glycol on immunogenicity and circulating life of bovine liver catalase. J. Biol. Chem. 252: 3582–3586; 1977.

[27] Duncan, R.; Spreafico, F. Polylmer Conjugates. Pharmacokinetics considerations for design and development. Clin. Pharmacokinet. 27: 290–306; 1994.

[28] Koshiishi, I.; Mamura, Y.; Liu, J.; Imanari, T. Degradation of dehydroascorbate to 2,3-diketogulonate in blood circulation. Biochim. Biophys. Acta. 1425: 209–214; 1998.

What is claimed is:

1. A method for depleting ascorbate in blood plasma extracted from a living body, by using ascorbate oxidase modified with biologically inert polymers.

2. The method for depleting ascorbate in blood plasma according to claim 1, wherein the biologically inert polymers are attached at sites other than the active sites.

3. The method for depleting ascorbate in blood plasma according to claim 1, wherein the biologically inert polymer is methoxypolyethylene glycol.

* * * * *